United States Patent [19]

Tsubota

[11] Patent Number: 6,159,930
[45] Date of Patent: Dec. 12, 2000

[54] PHARMACEUTICAL COMPOSITION COMPRISING ALBUMIN AS AN ACTIVE INGREDIENT

[75] Inventor: Kazuo Tsubota, Funabashi, Japan

[73] Assignee: R-Tech Ueno, Ltd., Osaka, Japan

[21] Appl. No.: 09/450,008

[22] Filed: Nov. 29, 1999

Related U.S. Application Data

[62] Division of application No. 08/981,229, Dec. 19, 1997, which is a continuation of application No. PCT/JP97/01329, Apr. 17, 1997, which is a continuation of application No. 08/752,928, Nov. 21, 1996, abandoned, and a continuation of application No. 08/752,941, Nov. 21, 1996, abandoned.

[30] Foreign Application Priority Data

Apr. 19, 1996 [JP] Japan ..................................... 8-098090
Apr. 26, 1996 [JP] Japan ..................................... 8-106866

[51] Int. Cl.[7] ................................................. A61K 38/00
[52] U.S. Cl. ................................................. 514/2; 514/912
[58] Field of Search ........................................ 514/2, 912

[56] References Cited

U.S. PATENT DOCUMENTS 4,775,531 10/1988 Gilbard ................................. 424/128

FOREIGN PATENT DOCUMENTS 5-310592  11/1993  Japan .
6-271478   9/1994  Japan .
93-64188   9/1994  Japan .

OTHER PUBLICATIONS

Chemical Abstracts 122:38840. Tsuboto et al, 1994.
Database Drugu, AN 84–16297. Koning et al. Combination Therapy for Dendritic Keratitis with Acyclovir and Alpha—Interferon. Arch. Ophthalmol. 101(12), 1866–68 (Dec. 1983).
Gupta et al. Trypsin and Serum Albumin in Tear Fluids in Acute Adenovirus Conjunctivitis. BR. J. Ophthalmol 72(5), 390–393 (May 1988).
Pedersen et al. The origin of immunoglobulin G in bovin tears. Acta Path. Microbiol.Scand.Set.B, 81B/12, 245–252 (Feb. 1973).
Zavaro et al. Proteins in Tears from Healthy and Diseased Eyes. Symposium on Uveal Melanomes, Nov. 24, 1979. Doc Ophthalmol 50(1) (Recd. 1981). 185–199 (Jan. 1981).
Ran S et al. Topical Plasma Fibronectin Compared to Albumin and Saline for Wond Healing of Denervated Ophthalmology, Sarasotata, Florida, USA, Apr. 3. (Mar. 1989).

*Primary Examiner*—Zohreh Fay
*Attorney, Agent, or Firm*—Sughrue, Mion, Zinn, Macpeak & Seas, PLLC

[57] ABSTRACT

The present invention provides a pharmaceutical composition for treatment of corneal and conjunctival lesion, and dry eye comprising albumin as an active ingredient. The pharmaceutical composition is also useful for increase of eye surface epithelium mucin secretion. The present invention further provides a method for treatment of corneal and conjunctival lesion and dry eye, which comprises administering, to a subject in need of such treatment, albumin in an amount effective. In addition, the present invention provides a use of albumin for manufacture of a pharmaceutical composition of the present invention.

4 Claims, No Drawings

PHARMACEUTICAL COMPOSITION COMPRISING ALBUMIN AS AN ACTIVE INGREDIENT

This is a division of application Ser. No. 08/981,229 filed Dec. 19, 1997, which is a continuation of PCT/JP97/01329, filed Apr. 17, 1997, which continued from U.S. application Ser. No. 08/752,928, filed Nov. 21, 1996, now abandoned, and U.S. application Ser. No. 08/752,941, filed Nov. 21, 1996, now abandoned and which PCT application embodies the subject matter of said U.S. applications.

Priority is claimed from Apr. 19, 1996, and Apr. 26, 1996, based on JAPAN application Nos: 098090/1996, and 106866/1996, respectively, and from U.S. application Ser. Nos. 08/752,928 and 08/752,941, both filed Nov. 21, 1996. The priority document(s) were filed in parent application Ser. Nos. 08/752,941 and 08/752,928.

TECHNICAL FIELD

The present invention provides a pharmaceutical composition comprising albumin as an active ingredient. The composition of the present invention is useful for treatment of the conditions such as corneal and conjunctival lesion and dry eye. The composition of the present invention has an ability to increase eye surface epithelium mucin secretion and also has an ability to diffuse oil. The present invention further provides methods for treatment of corneal and conjunctival lesion, treatment of dry eye conditions, and increase of eye surface epithelium mucin secretion using the composition.

BACKGROUND ART

Corneal and conjunctival lesion is caused by forming defects from the surface to epithelium. The cause may include pathogenic factors such as keratoconjunctivitis sicca (dry eye), various keratoconjunctivitis, allergy and infection of microorganisms (e.g. virus, bacteria, fungus, etc.), chemical factors such as cytotoxicity by chemicals and corrosion due to acid and alkaline, physical factors such as xerophthalmia, injury due to foreign matter (e.g. contact lens, etc.) and hot water, and the like. It has recently been reported that antiseptics contained in an ophthalmic composition (e.g. benzalkonium chloride, chlorobutanol, etc.) and ophthalmic agents (e.g. aminoglycoside antibiotics, non-steroidal anti-inflammatory drugs, IDU, pimaricin, etc.) cause a lesion of corneal epithelium (ectocornea).

For the present, in order to treat the corneal and conjunctival lesion, chondroitin sulfate, glutathione, hyaluronic acid, fibronectin, EGF, and the like are administered or an artificial tear solution is also administered for the purpose of replenishing a tear solution, but the effect of these treatments is not yet sufficient.

Dry eye is defined as a condition with decrease or change in quality of tear, irrespective of the presence or absence corneal and conjunctival lesion (Yamada et al. *GANKI* 43, 1289–1293(1992)). There are various factors for causing the dry eye, but no suitable method to recover the decreased amount of tear normal has been found yet.

For the present, in order to treat the dry eye, an artificial tear solution for the purpose of replenishing tear, and chondroitin sulfate, glutathione, hyaluronic acid, fibronectin, EGF, and the like for the purpose of relieving subjective symptoms are administered, but the effects are not yet sufficient.

From the recent investigation, it is believed that normal eye surface epithelium expresses mucin-like glycoproein and that said glycoprotein takes an active part in maintaining tear film. Furthermore, mucin secreted from conjunctival germ cells has been known to be responsible to stabilize tear film. So, defect of eye surface epithelium caused by any factor may induce abnormal eye mucin secretion and thereby unstable tear film. The unstable tear film may lower the interaction level between the epithelium and the tear film, and thereby the lesion of corneal and conjunctival epithelium may become worse (Norihiko Yokoi in "*GANKA. CHIRYO NO KOTSU TO OTOSHIANA* (Techniques for treatment in Ophthalmologic field), edited by FUMIO KOGURE, published by KABUSHIKI KAISHA NAKAYAMA SHOTEN, Tokyo, Japan pages 26–27 (1995)). From these points of view, it is suggested that conditions such as corneal and conjunctival lesion or dry eye can be treated if the tear film is stabilized by increasing mucin secretion or any other mean.

Albumin is a protein that exists widely in an animal/vegetable tissue or a body fluid, such as human serum, tear solution. For example, the human serum albumin is used for treating hypoalbuminemia, hemorrhagic shock, and the like. In the ophthalmic field, it is also known to use as a stabilizer for protein preparations such as fibronectin or interferon. It has been proposed to use the preparations such as fibronectin and interferon for treating corneal lesion (Japanese Patent Kokai No. Sho 61-103838 and No. Hei 6-271478), but there is no knowledge that albumin itself is effective for treating corneal and conjunctival lesion or dry eye.

DISCLOSURE OF INVENTION

The present invention provides a pharmaceutical composition for ophthalmology comprising albumin as an active ingredient. The present composition is useful for treating corneal and conjunctival lesion. The present composition also useful for treating dry eye.

The origin of albumin used for the composition of the present invention is not specifically limited. When albumin has an antigenicity, however, a problem such as allergy arises and, therefore, it is not preferred. Human origin albumin, e.g. human serum albumin is preferably used.

Human serum albumin, which is purified to the purity suitable for using normally in medical applications, can preferably be used in the present invention without any particular problem. That is, those containing not less than 80% of albumin (in case of analyzing with the electrophoresis) are preferred. In order to inactivate virus, etc., those obtained by heat-treating are preferred. Particularly, human serum albumin, which is commercially available as a drug, is preferably used.

Albumin produced by microorganism obtained by gene recombination is also preferably used in the present invention. The manufacturing method according to the gene recombination technique is well known to persons skilled in the art. Briefly explaining, a vector containing a gene coding a desired albumin (e.g. human albumin) may be introduced into a host cell to transform it. The transformed cell producing the desired protein may be selected and cultured, then, human albumin may be isolated and purified from the cultured supernatant or cell extract. Examples of the host cell include yeast, *Escherichia coli,* and the like, which are used ordinary by persons skilled in the art so as to produce a protein. In view of avoiding a risk of inclusion of virus, etc., albumin as a product of such gene recombination is more preferred.

As used herein, the term "corneal and conjunctival lesion" includes corneal and conjunctival lesion caused by pathogenic factors such as keratoconjunctivitis sicca (dry eye), various keratoconjunctivitis, allergy and infection of microorganisms (e.g. virus, bacteria, fungus, etc.), chemical factors such as cytotoxicity by chemicals and corrosion due to acid and alkaline, physical factors such as xerophthalmia, injury due to foreign matter (e.g. contact lens, etc.) and hot water, and the like, antiseptics contained in an ophthalmic composition (e.g. benzalkonium chloride, chlorobutanol, etc.) and ophthalmic agents (e.g. aminoglycoside antibiotics, non-steroidal anti-inflammatory drugs, IDU, pimaricin, etc.); defects of ectocornea; corneal erosion; corneal ulcer, and the like.

As used herein, the term "dry eye" includes not only simple dry eye (tear decrement) defined as "a condition with decrease or change in quality of tear, irrespective of the presence or absence of corneal and conjunctival lesion" but also various dry eye condition such as alacrima, xerophthalmia, Sjögren syndrome, dry keratoconjunctivitis, Stevens Johnson syndrome and ocular pemphigoid, blepharitis. Further, the term "dry eye" includes dry eye after cataract operation and that accompanied with allergic conjunctivitis, as well as dry eye like condition such as a tear decrement of VDT (Visual Display Terminal) worker and a tear decrement without any systemic symptom caused by, for example, dry room due to air conditioning.

As used herein, the term "treatment" or "treating" refers to any means of control of the conditions, including prevention, cure and relief of the conditions and arrestation or relief of development of the condition.

The inventor further found that albumin increases eye surface epithelium mucin secretion. Therefore, the present invention further provides a pharmaceutical composition for increasing eye surface mucin secretion comprising albumin as an active ingredient.

The inventor further found that albumin has a surfactant activity to diffuses oils. It is suggested that such surfactant activity of albumin contribute to eye surface tear film stabilization.

The pharmaceutical composition of the present invention may be in a dosage forms such as tablets, pills, powders, suspensions, capsules, suppositories, injection preparations, ointments, eye drops, and the like. It is particularly preferred to locally administer eye drops.

In case of the composition of the present invention is formulated as eye drops, the composition may contain albumin in an amount of about 1 to 1000 mg/ml, more preferably about 10 to 1000 mg/ml, further preferably about 50 to 1000 mg/ml. The composition may further contain a pharmaceutically acceptable diluent.

As used herein, the "pharmaceutically acceptable diluent" may be any diluent which is used for ophthalmic composition known to persons skilled in the art, for example, water, physiological saline, artificial tear solution, and the like.

The pharmaceutical composition of the present invention may further comprise various components that used in a normal ophthalmic composition, such as stabilizers, sterilizers, buffering agents, isotonic agents, chelating agents, pH adjusters, surfactants, and the like.

Examples of the stabilizer include normal L-type amino acids such as glycine and alanine, and the like, monosaccharides such as glucose and mannose, and the like, disaccharides such as sucrose and maltose, and the like, sugar alcohols such as mannitol and xylitol, and the like, and polysaccharides such as dextran, and the like.

Examples of the sterilizer include benzalkonium salt, chlorhexidine salt and ester of paraoxybenzoate, and the like.

Examples of the buffering agent include boric acid, phosphoric acid, acetic acid, and citric acid or a salt thereof.

Examples of the isotonic agent include sodium chloride, potassium chloride and saccharides, and the like.

Examples of the chelating agent include sodium edetate and citric acid, and the like.

Since it is an ophthalmic composition, pH is preferably adjusted from 5 to 8.

The composition may be administered in a dosage of about 1 to 100 μl/eye, preferably about 10 to 50 μl/eye, and more preferably about 30–50 μl/eye.

In an another aspect, the present invention also provides a use of albumin for manufacture of a pharmaceutical composition of the present invention.

In still further aspect, the present invention provides a method for treatment of corneal and conjunctival lesion, which comprises administering, to a subject in need of such treatment, albumin in an amount effective.

As used herein, the term "a subject in need of such treatment of corneal and conjunctival lesion" includes both of a patient who is actually suffered from corneal and conjunctival lesion and a patient suspected to be suffered from such lesion. It includes not only the patient whose corneal and conjunctival lesion has been actually recognized but also the patient who is suspected of corneal and conjunctival lesion and the patient in the state where a high possibility of occurring the condition such as a patient after keratoplasty.

In still further aspect, the present invention provides a method for treatment of dry eye, which comprises administering to a subject in need of such treatment, albumin in an amount effective. As used herein, the term "a subject in need of such treatment of dry eye" includes both of a patient who has the dry eye condition and a patient who suspected to be suffered from dry eye.

In these methods of the present invention, albumin may be the same as that employed in the above-described composition.

In these methods of the present invention, albumin may be administrated as the pharmaceutical composition of the present invention. The administration route is not limited but topical administration to eye is most preferable.

In these methods of the present invention, "the effective amount" of albumin, which is an amount for the desirable treatment, may be selected an optimum according to the patient's symptoms, age, sex, body weight, diet, other drugs used in combination and various factors which are recognized by persons skilled in the medical field. This effective amount may also vary depending on kind or activity of albumin, in addition to the above factors. Determination of the effective amount is an operation, which is usually conducted by persons skilled in the art of the medical field.

In these methods of the present invention, the pharmaceutical composition may be administered in a dosage of about 1 to 100 μl/eye, preferably about 10 to 50 μl/eye and more preferably about 30 to 50 μl/eye, about 1 to 20 times per day and more preferably, about 5 to 10 times per day, it is not intended to limit the scope of the invention.

In these methods of the present invention, the artificial tear solution, which has hitherto been used for treating corneal and conjunctival lesion or dry eye, may be administered together with albumin. In such a case, the artificial tear solution may be administered in the amount and schedule as usual.

In still further aspect of the present invention, the present invention provides a method for increase of eye surface epitherium mucin secretion, which comprises administering, to a subject in need of such administration, albumin in an amount effective. According to the present method, mucin secretion of the eye surface epithelium may be increased, and thereby, eye surface tear film may be stabilized.

As used herein, the "a subject in need of such administration" includes both of a patient with abnormal eye surface mucin secretion and a patient suspected to have abnormal eye surface mucin secretion due to deficient of eye surface epithelium, such as a patient of dry eye or corneal and conjunctival lesion.

In this method of the present invention, albumin may be administrated as the pharmaceutical composition of the present invention. The administration route is not limited but topical administration to eye is most preferable.

In this method of the present invention, "the effective amount" of albumin, which is an amount for increase eye surface mucin secretion, may be selected an optimum amount according to the patient's symptoms, age, sex, body weight, diet, other drugs used in combination and various factors which are recognized by persons skilled in the medical field. This effective amount may also vary depending on kind or activity of albumin, in addition to the above factors. Determination of the effective amount is an operation, which is usually conducted by persons skilled in the art of the medical field.

In this method of the present invention, the pharmaceutical composition may be administered in a dosage of about 1 to 100 μl/eye, preferably about 10 to 50 μl/eye and more preferably about 30 to 50 μl/eye, about 1 to 20 times per day and more preferably, about 5 to 10 times per day, it is not intended to limit the scope of the invention.

In this method of the present invention, the artificial tear solution, which has hitherto been used for treating corneal and conjunctival lesion or dry eye, may be administered together with albumin. In such a case, the artificial tear solution may be administered in the amount and schedule as usual.

FORMULATION EXAMPLE

In the examples of this application, donated blood albumin preparations manufactured by The Green Cross Corporation (Osaka, Japan) were used. These albumin preparations were obtained by using an albumin fraction which was isolated/purified plasma of a blood donar as a raw material according to a Cohn, cold ethanol fractionation method, preparing according to the following Formulation Example 1 and 2, and heat-treating at 60° C. for 10 hours.

| Formulation Example 1 | |
|---|---|
| (Albumin content: 25%) | |
| Human serum albumin | 250 mg/ml |
| Acetyltriptophan sodium | 5.37 mg/ml |
| Sodium caprylate | 3.32 mg/ml |
| Formulation Example 2 | |
| (Albumin content: 5%) | |
| Human serum albumin | 50 mg/ml |
| Acetyltriptophan sodium | 1.07 mg/ml |
| Sodium caprylate | 0.66 mg/ml |

TEST EXAMPLE 1

Three dry eye patients with corneal and conjunctival lesion (female aged 64, female aged 61 and female aged 34) were administrated to their eyes with 25% human serum albumin (albumin content: 250 mg/ml) of Formulation Example 1, 10 times per day with a dosage of 30 to 50 μl/eye. Together with administration of albumin, an artificial tear solution was also administered to the eyes.

An intravital stain examination was conducted before and after the administation to estimate the degree of corneal and conjunctival lesion. As the intravital stain examination, rose bengal staining and fluorescein staining were conducted. The rose bengal staining (RB) provides an index of corneal and conjunctival lesion, and scoring was conducted by estimating the degree of staining of nasal and aural sides of bulbar conjunctiva and cornea, by a score of 0–3 (total scores of 9). The fluorescein staining (F) provides an index of corneal lesion, and scoring was conducted by estimating the degree of corneal lesion by a score of 0–3. In both cases, scoring was conducted according to a van Bijsterreld's evaluation method. In both cases, the higher the numerical value is, the more severe the lesion is. The results are shown in Table 1.

TABLE 1

| | Effect of albumin administration | | | | |
|---|---|---|---|---|---|
| Patient | Female aged sixty-four 14 Days | | Female aged sixty-one 14 days | | Female aged thirty-four* |
| Administration period | Right eye | Left eye | Right eye | Left eye | 7 days |
| RB | | | | | |
| Before administration | 7 | 7 | 8 | 8 | The superior limbic part is strongly stained. |
| After administration | 3 | 3 | 5 | 5 | The superior limbic part is scarcely stained. |
| F | | | | | |
| Before administration | 2 | 2 | 3 | 2 | The superior limbic part is strongly stained. |
| After administration | 1 | 1 | 1 | 1 | The superior limbic part is scarcely stained |

*She was suffered from superior limbic keratoconjunctivitis in addition to the dry eye.

TEST EXAMPLE 2

Male aged 62 with defects of ectocornea after keratoplasty

After penetrating keratoplasty of the right eye, defects of ectocornea were continued and 0.1% Hyaleinmini (trademark) (containing 0.1% of hyaluronic acid) was administered. However, no effect was observed and, therefore, administration of 0.1% Hyaleinmini was terminated. Thereafter, 25% human serum albumin (albumin content: 250 mg/ml) of Formulation Example 1 was administered to the eyes 10 times per day with a dosage of 30 to 50 μl/eye for one week. One week after the beginning of administration, ectocornea is formed and defects of ectocornea were improved.

TEST EXAMPLE 3

Female aged 64 with defects of ectocornea after keratoplasty

After penetrating keratoplasty of the left eye, limbus transplantation and amnion transplantation, defects of ectocornea were detected by the fluorescein staining. To the eyes of this patient, 5% human serum albumin (albumin content: 50 mg/ml) of Formulation Example 2 was administered 10 times per day with a dosage of 30 to 50 μl/eye for four weeks. Two weeks after the beginning of the administration, fluorescein staining showed improvement in defects of ectocornea. Four weeks after the beginning of the administration, no staining was observed and an apparent improvement in defects of ectocornea was recognized.

TEST EXAMPLE 4

Female aged 72 with Sjögren syndrome

To the eyes of the patient with defects of ectocorneal accompanied with Sjögren syndrome, Intal (trademark) (containing sodium cromoglicate), 0.1% Flumetholon (trademark) (containing fluorometholone) and an artificial tear solution were administered. However, no improvement in defects of ectocornea was observed and the administration was terminated. Then, to the eyes of the patient, 5% human serum albumin (albumin content: 50 mg/ml) of Formulation Example 2 was administered 6 times per day with a dosage of 30 to 50 μl/eye for four weeks. Four weeks after the beginning of the administration, defects of ectocornea were not observed.

TEST EXAMPLE 5

Female aged 45 with Sjögren syndrome

To the eyes of the patient with corneal and conjunctival lesion accompanied with Sjögren syndrome, 5% human serum albumin (albumin content: 50 mg/ml) of Formulation Example 2 was administered 10 times per day with a dosage of 30 to 50 μl/eye for four weeks.

Before and after the administration, an intravital stain examination (rose bengal staining and fluorescein staining) was conducted to estimate the degree of corneal and conjunctival lesion. The intravital stain examination was conducted by applying 2 μl of a mix solution containing 1% rose bengal and 1% fluorescein to the lower eyelids of the patient using a micro-pipette accurately, making the patient to blink several times, and then observing the eyes. Rose bengal staining (RB) was measured with white light of slit lamp and fluorescein staining (F) was measured with cobalt blue light. The extent of staining was scored from 0 to 9. The results are shown in Table 2.

TABLE 2

Effects of albumin administration

| | | before administration | After administration (four weeks) |
|---|---|---|---|
| RB score | right eye | 7 | 2 |
| | left eye | 7 | 2 |
| F score | right eye | 9 | 2 |
| | left eye | 9 | 2 |

TEST EXAMPLE 6

Three dry eye patients (female aged 64, female aged 6 L and female aged 34) were administrated with 25% human serum albumin (albumin content: 250 mg/ml) of Formulation Example 1 to their eyes 10 times per day with a dosage of 30 to 50 μl/eye. Together with administration of albumin, an artificial tear solution was also administrated to the eye.

Before and after the administration, subjective symptoms of the patients were estimated and scored. The subjective symptom includes eye ache, eye dry feeling and eye foreign body feeling. Estimation of the symptoms was made by the patients themselves. The worst subjective symptom was scored as 100 point and best or normal as 0. The results are shown in Table 3.

TABLE 3

Improvement of subjective symptoms by administration of album

| Patient term of administration | Female, aged 64 14 days | | Female, aged 61 14 days | | Female, aged 34* |
|---|---|---|---|---|---|
| | right eye | left eye | right eye | left eye | 7 days |
| before administration | 100 | 100 | 100 | 100 | 100 |
| after administration | 0 | 30 | 50 | 50 | 20 |

*she was suffered from superior limbic keratoconjunctivitis in addition to the dry eye.

TEST EXAMPLE 7

To the eyes of a dry eye patient accompanying with Sjögren syndrome (female aged 74), 5% human serum albumin (albumin content: 50 mg/ml) of Formulation Example 2 was administered 6 times per day with a dosage of 30 to 50 μl/eye for eight weeks.

After eight weeks, subjective symptoms including eye ache, eye dry feeling and eye foreign body feeling were almost perfectly removed. Administration of albumin was stopped.

TEST EXAMPLE 8

The ability of albumin to increase mucin secretion of eye epitherium was investigated.

CCL cells (conjunctival epitherium cell strain) were cultured in TCM199 medium (GIBCO) containing 10% (w/v) human serum albumin (SIGMA) for 24 hours according to conventional cell culture condition. As a culture control, the cells were cultured with the TCM 199 medium without human serum albumin.

The cultured cells were harvested from the culture vessel using trypsin-EDTA, fixed with paraformaldehyde for 30 minutes and washed with phosphate buffered saline (PBS)

three times. The obtained cells were blocked (4° C., 30 min.) with normal goat: serum and the blocked cells were reacted (4° C., 30 min.) with mouse anti-mucin antibody (Muc 1), and then washed with PBS three times. The cells further reacted (4° C., 30 min.) with FITC-labeled anti-mouse IgG antibody and then washed three times with PBS.

The obtained cells were measured with Epics (Colter Co.) by flow-cytometry method to determine the proportion (%) of mucin generating cells (positive cells) to the whole cells. The result is shown in Table 4.

TABLE 4 increase of mucin secretion by albumin

|  | mucin generating cells(positive) |
|---|---|
| control (without albumin) | 15.2% |
| cultured with 10% albumin | 35.5% |

According to the result, addition of albumin to the culture medium apparently increased mucin secretion ability of conjunctival epitherium.

TEST EXAMPLE 9

Ability to diffuse oil by albumin:

10 vol % of caster oil was added to an artificial tear solution. The oil and the solution separated out and oil drops were formed. In this system, 10% (v/v of artificial tear solution) of 5% albumin solution was added, the oil diffused over the surface of the water phase and the oil drops disappeared.

According to this example, it is suggested that albumin can act as a surfactant to protect vaporization of tear solution from eye surface.

INDUSTRIAL APPLICABILITY

The pharmaceutical composition, method and use of the present invention are useful for treatment of corneal and conjunctival lesion and dry eye. The pharmaceutical composition, method and use of the present invention are also useful for increasing mucin secretion of eye surface epitherium.

What is claimed is:

1. A method for treatment of corneal and conjunctival lesion which comprises administering, to a subject in need of such treatment, albumin in an amount effective.

2. The method according to claim 1, wherein the said albumin is human origin albumin.

3. The method according to claim 1, wherein the said albumin is administered in the form of eye drops.

4. The method according to claim 1, which comprises administering a pharmaceutical composition containing 1 to 1000 mg/ml of albumin and pharmaceutically acceptable carrier.

* * * * *